(12) United States Patent
Towler

(10) Patent No.: US 9,186,065 B2
(45) Date of Patent: *Nov. 17, 2015

(54) DIAGNOSTIC METHODS FOR OSTEOPOROSIS

(71) Applicant: Crescent Diagnostics Limited, London (GB)

(72) Inventor: Mark Robert Towler, Annacotty (IE)

(73) Assignee: Crescent Diagnostics Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/966,447

(22) Filed: Aug. 14, 2013

(65) Prior Publication Data
US 2013/0335729 A1    Dec. 19, 2013

Related U.S. Application Data

(63) Continuation of application No. 11/570,669, filed as application No. PCT/EP2005/006694 on Jun. 20, 2005, now Pat. No. 8,535,238.

(60) Provisional application No. 60/581,807, filed on Jun. 22, 2004.

(51) Int. Cl.
*A61B 5/00* (2006.01)
*G01J 3/44* (2006.01)

(52) U.S. Cl.
CPC .............. *A61B 5/0075* (2013.01); *A61B 5/0059* (2013.01); *A61B 5/441* (2013.01); *A61B 5/4504* (2013.01); *A61B 5/4509* (2013.01); *G01J 3/44* (2013.01)

(58) Field of Classification Search
CPC .... A61B 5/0075; A61B 5/441; A61B 5/4509; A61B 5/4504; G01J 3/44
USPC ...................................... 356/51, 301
See application file for complete search history.

(56) References Cited

U.S. PATENT DOCUMENTS

| | | | |
|---|---|---|---|
| 5,873,831 A | 2/1999 | Bernstein et al. | |
| 6,205,354 B1 | 3/2001 | Gellermann et al. | |
| 7,050,842 B2 | 5/2006 | Chaiken et al. | |
| 7,652,763 B2 | 1/2010 | Matousek et al. | |
| 7,962,199 B2 | 6/2011 | Carron et al. | |
| 2002/0002336 A1 | 1/2002 | Marchitto et al. | |
| 2002/0127711 A1 | 9/2002 | Kale et al. | |
| 2002/0169379 A1 | 11/2002 | Camacho et al. | |

(Continued)

OTHER PUBLICATIONS

Canadian Office Action from application 2,577,164 mailed Mar. 14, 2013 (3 pages).

(Continued)

*Primary Examiner* — Bo J Peng
(74) *Attorney, Agent, or Firm* — Brown Rudnick LLP; Thomas C. Meyers

(57) ABSTRACT

Methods of diagnosing bone disease such as osteoporosis are provided. The methods comprise detecting changes in the physical or chemical structure of a keratinized tissue as correlates of disease. The methods include detecting changes in the hardness, modulus, or level of sulfur bonding, particularly the level of disulfide bonding, in a keratinized tissue sample such as nail, hair, or skin. Changes in these variables serve as diagnostic markers of bone diseases that are associated with changes in bone elasticity and bone density.

10 Claims, 7 Drawing Sheets

(56) References Cited

U.S. PATENT DOCUMENTS

| | | |
|---|---|---|
| 2003/0208169 A1 | 11/2003 | Chaiken et al. |
| 2005/0010130 A1 | 1/2005 | Morris et al. |
| 2005/0187438 A1 | 8/2005 | Xie |
| 2009/0012403 A1 | 1/2009 | Carron et al. |
| 2009/0099458 A9 | 4/2009 | Towler et al. |
| 2012/0252050 A1 | 10/2012 | Towler et al. |

OTHER PUBLICATIONS

Feskanich, 1998, Use of toenail fluoride levels as an indicator for the risk of hip and forearm fractures in women, Epidemiology 9(4):412-416.

Gniadecka, et al., 1998, Structure of water, proteins, and lipids in intact human skin, hair, and nail, J Inv Derm 110 (4):393-8.

Hard as Nails, Jul. 3, 2003, The Economist (1 page).

Horan, 1982, The white nails of old age (Neapolitan nails), Am Ger Soc 30(12):734-737.

International Search Report for PCTUS2006025426 mailed Mar. 8, 2007 (4 pages).

New Test for Osteoporosis, 2003, Financial Times, London (1 page).

Oliver, 2004, Measurment of hardness and elastic modulus by instrumented indentation: advances in understadning and refinements to methodology, Mat Res Soc 19(1):3-20.

Pierard, 2001, Relationship between bone mass density and tensile strength in the skin of women, EJCI 31:731-735.

Pillay, et al., 2005, The use of fingernails as a means of assessing bone health: a pilot study, J Wom Health 14 (4):339-344.

Towler, 2003, Preliminary Work on the Development of a Novel Detection Method for Osteoporosis, Conference Proceedings, 18th European Conference on Biomaterials, Stuttgart, Germany, Oct. 1-4, 2003 (1 page).

Towler, Jun. 24, 2003, UL researchers develop new test of osteoporosis, University of Limerick press release (1 page).

Towler, 2004, Preliminary work on the development of a novel detection method for osteoporosis, Proc 7th World Biom Cong May 17, 2004-May 21, 2004, p. 1242 (1 page).

Who, 2003, technical report 921, Prevention and Treatment of Osteoporosis, World Health Organization, Geneva (206 pages).

Zhang, 2004, Mechanical properties of skeletal bone in gene-mutated Stopseldtl28d and wild-type zebrafish (Danio rerio) measured by atomic force microscopy-based nanoindentation, Bone 30(4):541-546.

Hansen, 2002, The Mechanical Properties of Skin in Osteogenesis Imperfecta, Archives of Dermatology 138 (7):909-911.

Robson, 1974, Hardness of finger nails in well-nourished and malnourished populations, British Journal of Nutrition 32:389-394.

Williams, et al., Raman spectra of human keratotic biopolymers: Skin, callus, hair and nail, J Raman Spectroscopy 25 (1):95-98, Note: this NPL has publication year 1994, cited in the parent application.

MSM, http://www.msmforless.com/benefits_msm.htm, Feb. 25, 2002 (3 pages).

Tarnowski, 2002, Mineralization of developing mouse calvaria as revealed by Raman microspectroscopy, JBMR 17 (6):1118-1126.

DIAGNOSTIC METHODS FOR OSTEOPOROSIS

CROSS-REFERENCE TO RELATED APPLICATION

This application is a continuation of U.S. patent application Ser. No. 11/570,669, filed Sep. 11, 2007, which is a national stage entry of International Patent Application Serial No. PCT/EP05/06694, filed on Jun. 20, 2005, which claims priority to U.S. Provisional Patent Application Ser. No. 60/581,807, filed on Jun. 22, 2004, the contents of each of which are incorporated by reference.

FIELD OF THE INVENTION

The present invention relates to methods of diagnosing osteoporosis by detecting physical and chemical changes in keratinized tissues.

BACKGROUND OF THE INVENTION

Osteoporosis is a disease characterized by a deficiency of bone that affects both the protein matrix and the mineral fraction, resulting in a decrease in the resistance of bones to fracture. The current method of diagnosis is by means of dual energy x-ray absorptiometry (DEXA), which provides a quantitative measurement of the amount of mineral present in bone and allows determination of fracture risk at a measured site. A decrease in bone mineral density (BMD) as measured by DEXA is the current method of diagnosing osteoporosis and predicting fractures. See, for example, Nevitt and Cummings (1993) *J. Am. Geriatr. Soc.* 41:1226; and Parfitt (1993) *Calcif. Tissue Int.* 53:S82. However, the lack of perfect correlation between bone mineral density and bone fractures suggests that low bone mineral density is not the only cause of fragile bones (Ott (1993) *Calcif. Tissue Int.* 53(Suppl.):S7). Thus, while the degree of mineralization is the current standard by which osteoporosis is diagnosed, it is unable to detect bone fragility due to deficiency in protein matrix.

Bone is a composite material, comprising mineral, organic, and water phases (Katz (1971) *J. Biomech.* 4:455). The mineral phase, mainly hydroxyapatite (HA), imparts compressive strength, while the organic phase, collagen, imparts flexibility. Wang et al. (1998) *Bone* 23:67 have shown that with increasing age, the fracture toughness of bone is decreased and its microhardness increased without significant changes in BMD. McCalden et al. reported similar findings, indicating that even without significant changes in BMD, the tensile strength of bone can decrease with age due to increased porosity (McCalden et al. (1993) *J. Bone Joint Surg.* 75A: 1193). There is now a belief that the organic phase of bone plays a significant role in osteoporosis. Kovach et al. have shown that changes in the structural characteristics of the collagen network detected using a laser fluorescence technique correlate significantly with bone fracture toughness (Kovach et al. (1997) *Proceedings of the 43th Annual Meeting of the Orthopaedic Research Society*, San Francisco, Calif., 22:37). This work is supported by other findings demonstrating that the organic phase of bone is responsible for much of its ability to resist fracture (Wang et al. (1998) *Proceedings of the 44th Annual Meeting of the Orthopaedic Research Society*, New Orleans, La.; and Wang et al. (2002) *Bone* 31:1). Mansell and Bailey found that collagen in osteoporotic bone is not normal but instead contains higher levels of lysine hydroxylation and modified cross-linking (Mansell and Bailey (2003) *Int. J. Biochem. Cell Biol.* 35:522). This and other studies have shown that osteoporosis has a degenerative effect on protein production in bones with increased immature collagen cross-links, increased collagen synthesis and degradation (increased turnover despite overall loss of collagen), as well as reduced mineralization (Oxlund (1996) *Bone* 19:479; and Bailey (2002) *J. Musculoskel. Neuron Interact.* 2:529). The increased hydroxylation leads to the formation of finer fibrils with altered crosslinks, and reduced calcification, which further contributes to the fragility of the bone.

One study examined the calcium and magnesium levels in bone and nails (Vecht-Hart et al. (1995) *Clin. Chim. Acta* 236:1). No correlation was found to exist between the two. Other research examined the relationship between mineral concentrations in nail and bone, and the results have suggested that significant correlations exist between zinc levels and BMD ($r=-0.399$) and between the ratio of Zn/Ca to BMD ($r=0.421$) (Karita and Takano (1994) *Nippon Koshu Eisei Zasshi* 41:759). Nevertheless, these assays all examine the inorganic component of bone and nails, and do not correlate changes in the protein chemistry or structure that may also be present in the disease state.

Bone densitometry is the current gold standard for diagnosis of bone diseases such as osteoporosis. However, this method is limited to measuring bone mass, and it does not take into consideration the microarchitecture of the bone, the crystal organization, size and shape, the connectivity of the trabecullar network, and the structure of the bone proteins. Moreover, DEXA is a relatively expensive diagnostic procedure that exposes the patient to potentially harmful x-rays; thus it cannot be used for mass screenings, such as at routine checkups. Therefore, clinicians risk under diagnosing patients at risk for fracture because the bone disease is often unrecognized until a fracture occurs, or because bone mineral density does not always correlate with a risk of fragile bones even when DEXA is used. The alternative of obtaining collagen from patient's bones is an even more expensive and risky procedure. Thus, clinicians need new, low-risk methods to diagnose patients that are at an increased risk of bone fracture.

BRIEF SUMMARY OF THE INVENTION

Methods useful in the diagnosis and prognosis of bone-related disorders such as osteoporosis are provided. The methods comprise measuring physical and chemical changes of keratinized tissue as markers for the presence of bone disease in a subject. The methods are especially useful for detecting osteoporosis and monitoring progression of bone disease. The methods disclosed herein can be also be used in prognostic assays prior to, during, and after disease therapy. The disclosed prognostic assays are also useful for identifying subjects as candidates for various preferred means of therapeutic intervention.

The methods of the present invention comprise detecting physical and chemical changes in keratinized tissue that are predictive of the presence of a bone disease that is associated with a change in bone elasticity or bone density. The physical and chemical changes include a reduction in the hardness of a keratinized tissue, a reduction in the modulus of a keratinized tissue, or a reduction in the level of sulfur bonding in a keratinized tissue. Methods of detecting changes in the hardness and modulus of keratinized tissue include measuring the nanoindentation pressure and deformation of a keratinized tissue such as nail, hair, or skin. Methods of detecting changes in the level of sulfur bonding in keratinized tissue include using spectral analysis such as Raman spectroscopy to identify the relative abundance of disulfide bonds and carbon sulfide bonds in a keratinized tissue such as nail, hair, or skin. The advantages of examining a keratinized tissue such as nail, hair, or skin lies in the ability to assess properties other than those measured by standard bone densitometry, the ease of access to such samples, and the rapid growth of keratinized tissue, which allows changes to be monitored on a more frequent basis.

DETAILED DESCRIPTION OF THE INVENTION

Figure 1:
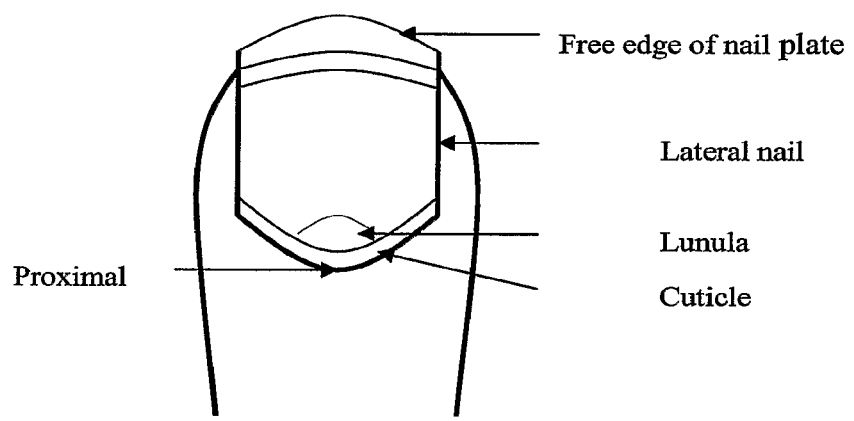
FIG. 1 shows a schematic of a human fingernail. The nail clippings used in Example 1 described herein were taken from the free edge of the nail plate.

The present invention is directed to methods for diagnosis and prognosis of bone disease in a subject, where the disease is associated with a change in bone elasticity or bone density. The methods rely on detection of physical and chemical changes in keratinized tissue as markers for the presence of the bone disease of interest in a subject.

Without being bound by any mechanism or theory of action, it has been found that physical and chemical changes within a keratinized tissue correlate to the presence or absence of bone disease that is associated with changes in bone elasticity or bone density, such as osteoporosis. By "bone disease that is associated with changes in bone elasticity or bone density" is intended to mean any disease where the risk of bone fracture is increased due to structural and chemical changes in the bone. Examples of such diseases include but are not limited to osteoporosis, osteogenesis imperfecta, Paget's disease, and the like. These structural and chemical changes in bone are measurable by any means known in the art including but not limited to measurement of bone mineral density (BMD) and bone biopsy. The structural and chemical changes in bone correlate to changes in the level of sulfur bonding of a keratinized tissue or changes in the hardness or modulus of such keratinized tissue. The term "keratinized tissue" is intended to mean any biological sample comprising the protein keratin, more particularly hard keratin. Keratinized tissue includes nail (fingernails and toenails), hair, skin (i.e., epidermis), and the like. Measurements on keratinized tissue samples may be made in situ (e.g., measurements made on the attached nail, hair, or skin sample, including but not limited to skin on the hand, foot, arm, leg, torso, or face) or by collecting the keratinized tissue sample (e.g., as clipped nails (also referred to as nail clippings), clipped hair, detached skin (i.e., epidermal peels or scrapings)) for measurement at a later time. The safety of obtaining keratinized tissue samples such as nail, hair, or skin, coupled with their diagnostic power independent of bone mineral density and bone biopsy make keratinized tissue-based diagnostic assays a useful new clinical tool.

The methods of the present invention generally comprise detecting changes in the physical or chemical structure of the keratinized tissue sample and correlating a change (or lack of change) with a diagnosis of bone disease. In some embodiments, the changes in physical or chemical structure of a keratinized tissue sample are used to assess whether the subject has osteoporosis or other bone disease that is associated with changes in bone elasticity or bone density and, thus, is at increased risk of bone fractures.

In other embodiments, the changes in physical or chemical structure of a keratinized tissue sample are used to assess the prognosis of a subject with osteoporosis or other bone disease that is associated with changes in bone elasticity or bone density. Because the presence or absence of reduced bone mineral density is not in perfect correlation with the risk of bone fracture, changes in the physical or chemical structure of keratinized tissue may be used to assess additional risk factors such as correlating the likely progression of disease and prognosis of a subject at increased risk of fracture.

Physical and chemical markers of interest include changes in the hardness or modulus of a keratinized tissue or changes in the level of sulfur bonding within the keratinized tissue. Methods for detecting changes in hardness or modulus of a keratinized tissue are well known in the art and include but are not limited to nanoindentation and atomic force microscopy. Methods for detecting changes in the level of sulfur bonding within a keratinized tissue are also well known in the art and include but are not limited to Raman spectroscopy, nuclear magnetic resonance spectroscopy, Fourier transform infrared (FT-IR) spectroscopy, chiroptical techniques, mass spectroscopy, chromatography, reaction with other chemicals such as Elman's reagent, and the like. See, for example, Walker (2002) *The Protein Protocols Handbook* (Humana Press, Totowa). Those skilled in the art recognize that the diagnostic power of the variables disclosed herein is not limited to a particular method of detection of the variable or changes thereof.

Keratin molecules are helical and fibrous. They form intermediate filaments by twisting around each other to form strands. Keratin contains a high percentage of sulfur-containing amino acids, largely cysteine. These cysteines form disulfide bridges between the individual molecules. The bridges cross-link the various secondary, tertiary, and quaternary keratin structures and thereby help maintain the structural rigidity of keratinized tissue. "Hard" keratin, such as that in hair, nails, and skin (particularly the epidermal layer) has a greater amount of structural rigidity due to more disulfide bonds.

As disclosed herein, changes in hardness, modulus, or level of sulfur bonding of a keratinized tissue are correlated to bone disease. Therefore, changes in these physical and chemical properties of keratinized tissue may be used as diagnostic markers for bone diseases that are associated with changes in bone elasticity and bone density. In one embodiment of the invention, a change in the hardness of a keratinized tissue is used to diagnose a patient with bone disease. In other embodiments, a change in the modulus of a keratinized tissue is used to diagnose bone disease. In yet other embodiments, a change in the level of sulfur bonding in a keratinized tissue is used to diagnose bone disease.

Modulus and hardness are measures of the brittleness of a keratinized tissue, for example, nails, hair, or skin. By "modulus" is intended stiffness or resistance of a keratinized tissue sample to deformation. By "hardness" is intended the extent to which a keratinized tissue sample is resistant to pressure. By "level of sulfur bonding" is intended the extent of the reduction (or, reciprocally, oxidation) of sulfur-containing amino acids such as cysteine and methionine, more specifically the extent to which the proteins form disulfide bridges or carbon sulfide bonds.

The presence, absence, or extent of change in hardness, modulus, or level of sulfur bonding of a keratinized tissue sample, such as nails, hair, or skin, can be correlated to the presence, absence, or extent of bone disease using methods standard in the art. See, for example, Zhou et al. (2002) *Statistical Methods in Diagnostic Medicine* (Wiley, New York). In one embodiment, the hardness of a keratinized tissue such as nails, hair, or skin provides a diagnostic criterion for bone fragility and osteoporosis. In another embodiment, the modulus of a keratinized tissue such as nails, hair, or skin provides a diagnostic criterion for bone fragility and osteoporosis. In other embodiments, the level of sulfur bonding within a keratinized tissue such as nails, hair, or skin provides a diagnostic criterion for bone fragility and osteoporosis. In further embodiments, the hardness, the modulus, or the level of sulfur bonding in a keratinized tissue such as nails, hair, or skin is used in combination with other diagnostic criteria previously known in the art such as bone mineral density tests (e.g., DEXA scans) and other previously known clinical correlates to disease. As previously noted, measurements on keratinized tissue samples may be made in situ (e.g., measurements made on the attached nail, hair, or skin sample) or by collecting the keratinized tissue sample (e.g., as clipped nails (also referred to as nail clippings), clipped hair, detached skin (i.e., epidermal peels or scrapings)) for measurement at a later time.

In one embodiment, the hardness or modulus of a keratinized tissue sample is measured by a method termed "nanoindentation" using a machine previously described by Arteaga et al. (1993) *Tribology Intl.* 26:305. In this method, force is applied to a keratinized tissue sample and the resistance measured. In one such embodiment, the keratinized tissue sample is nails (fingernails or toenails), either attached (i.e., measurement performed in situ) or clipped. Where nail clippings are to be measured, the nail clippings are collected from the free edge of the nail plate as shown in FIG. 1. Following collection, nanoindentation is used to detect hardness or modulus of the nail clippings. Preferably the nail clippings are subjected to nanoindentation within 1 day to within one month of collection, more preferably within 1 day to within three weeks of collection. In some embodiments, the nail clippings are subjected to nanoindentation within 1 day to within two weeks of collection; in other embodiments, the nail clippings are subjected to nanoindentation within 1 day to within one week, preferably within 1 day to within 3 days of collection. Where nail clippings are to be stored for future analysis, they are collected and stored in sealed jars to minimize changes in hydration following nail clipping collection.

Following collection of the nail clippings, the clippings are subjected to nanoindentation to assess hardness and modulus of this keratinized tissue. More specifically, pressure and release cycle readings are taken of the displacement of the indenter δ, and the load P, allowing the examination of force-penetration data during both the loading and unloading phases. A curve measuring the penetration depth at each force level during the loading and unloading phases can then be generated.

Figure 2:
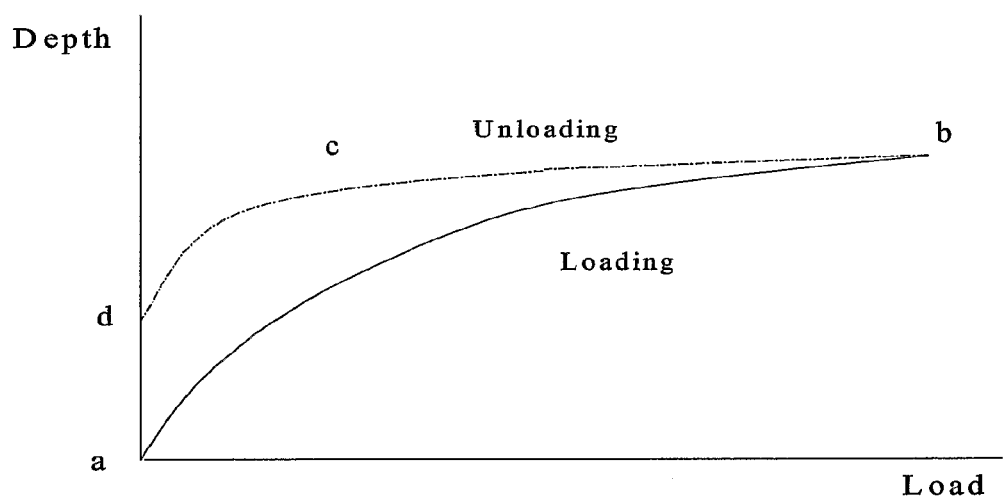
FIG. 2 shows a schematic representation of a typical nanoindentation curve comprising loading (a-b) and unloading (b-c-d) phases.

In this manner, the modulus can be defined as the linear section of the nanoindentation unloading curve (b-c in FIG. 2).

In some embodiments, the hardness, H, is defined as $$H = \frac{P}{A} \tag{Formula 1}$$

where P is the force applied to the indenter and A is the projected area of the contact. In nanoindentation, the projected area of contact is calculated from the geometry of the indenter and the measured depth of penetration in contact with the indenter, h, using the machine disclosed by Arteaga et al. (1993) *Tribology Intl.* 26:305, where $$A = kh^2 \tag{Formula 2}$$

and where k is a constant dependant upon the geometry and type of indenter used. In some embodiments, the indenter is a trigonal diamond pyramid with an equilateral triangular cross-section and a 90° angle between each face and the opposing edge (the corner of a cube). For this indenter k=2.6. Substituting (Formula 2) into (Formula 1) gives:

$$H = \frac{P}{2.6 \cdot \delta_p^2} \tag{Formula 3}$$

While the indenter is moving into the material, the load P has to provide the stress field which is necessary to support the plastic flow of material out of the indentation as well as the static pressure equal to the hardness. Due to this, the curve of dynamic hardness as a function of depth derived from (Formula 1) usually has a very high value at small depths where the strain rate, which is proportional to 1/δ dδ/dt, is greatest. In some embodiments, a single hardness number is quoted from the results and this is taken as the maximum applied force where the strain rate is a minimum.

Though the foregoing discussion of nanoindentation is directed to nail clippings, the methodology is also applicable to attached nails, as well as to other keratinized tissues including hair and skin, which can be measured in situ or on collected tissue samples that are handled in a manner similar to that described above for nail clippings. In this manner, keratinized tissue is collected, for example, clipped hair or detached skin tissue, and the collected tissue sample is subjected to nanoindentation within 1 day to within one month of collection, more preferably within 1 day to within three weeks of collection. In some embodiments, the keratinized tissue is collected and the collected tissue sample is subjected to nanoindentation within 1 day to within two weeks of collection; in other embodiments, the keratinized tissue is collected and the collected tissue sample is subjected to nanoindentation within 1 day to within one week, preferably within 1 day to within 3 days of collection. As previously noted above for nail clippings, where keratinized tissue is to be stored for future analysis, tissue samples are collected and stored in sealed jars to minimize changes in hydration following tissue collection.

In another embodiment, level of sulfur bonding within a keratinized tissue such as nails, hair, or skin is measured, either in situ or following collection of the keratinized tissue sample. Of particular interest is the extent of disulfide bridge formation between cysteine molecules in the keratinized tissue. The extent of crosslinking of cysteine via oxidized thiols (also known as the formation of cystine) correlates with the hardness or modulus of keratinized tissue as discussed supra. In one such embodiment, the extent of disulfide bridge formation is measured by means of spectral analysis, for example, using Raman spectroscopy, nuclear magnetic resonance spectroscopy, FT-IR spectroscopy, chiroptical techniques, mass spectroscopy, chromatography, reaction with other chemicals such as Elman's reagent, and the like.

Raman spectroscopy is a widely used tool for qualitative and quantitative analysis of materials. It relies on a spectral shift that occurs when light is projected onto a material to be tested and then deflected off the material surface. In laser Raman spectroscopy, monochromatic laser light that is deflected or scattered off the test material surface is detected by a sensitive detection system. The majority of the light deflected off the surface is scattered elastically at the same wavelength as the original light source in a process known as Rayleigh scattering. The remainder of the deflected light is scattered inelastically at a wavelength that differs from the original light source in a process known as Raman scattering. The two types of scattered light are separated from each other using any suitable wavelength selection system, such as prisms, filters, or optical gratings. The resulting Raman spectrum can be used to identify and quantify concentrations of various substances within the test material of interest. Raman scattering detected from a keratinized tissue sample can be used to identify individuals having or at risk of developing a bone disease such as osteoporosis.

In this manner, a keratinized tissue sample, such as nail (i.e., fingernail or toenail), hair, or skin (measured in situ or on a tissue sample collected as described above) is irradiated by a light source such as a laser, and then the wave number and intensity of the inelastically scattered light is measured. In one embodiment, the keratinized tissue sample is nail. Raman spectra of human nails are known (Akhtar and Edwards (1997) *Spectrochimica Acta A*53:81; and Edwards et al. (1998) *Spectrochimica Acta* A54:745). The Raman spectra reflect the bonding arrangements in the molecular makeup of a keratinized tissue such as nail, hair, or skin. Although the Raman spectrum can cover between 300 $cm^{-1}$ and 1800 $cm^{-1}$, particular peaks in this spectrum correspond to specific chemical structures of interest to the methods of the present invention. For sulfur bonding, the area of interest is generally between 400 $cm^{-1}$ and 700 $cm^{-1}$. For example, in human nails, three peaks correspond to sulfur bonds present in keratin, the most abundant protein in nails, specifically the disulfide bond (S-S, gauche-gauche-gauche conformation) at 510 $cm^{-1}$ and the carbon sulfide bond (C-S) at about 621 $cm^{-1}$ and 643 $cm^{-1}$. These Raman spectra can be used alone or in combination to indicate the extent to which cysteine is oxidized to form disulfide bridges in a keratinized tissue sample.

Thus, in some embodiments, the Raman spectra measurements are conducted on nails (i.e., fingernails or toenails) in situ or on nail clippings. Any Raman spectroscopy apparatus known in the art can be used to analyze the nails. See, for example, the non-invasive Raman spectroscopy apparatus for in situ measurements of carotenoid levels in living tissues described in U.S. Pat. Nos. 5,873,831 and 6,205,354, herein incorporated by reference in their entirety, and a modification of this apparatus as described in Example 3 herein below. Such an apparatus specifically designed for non-invasive measurement of sulfide bond levels in a keratinized tissue sample such as nails, particularly the level of disulfide bonding corresponding to the peak appearing at 510 $cm^{-1}$ of the Raman spectrum, comprises the following components: (1) a means for generating light within a wavelength giving a Raman response with a wavelength shift for the disulfide bond to be detected; (2) a delivery means for directing this light onto the fingernail, where this light has an intensity that does not damage the fingernail and does not alter disulfide bond levels; (3) a collection means for collecting light scattered from the fingernail; (4) spectrally selective means for selecting Raman shifted light from the scattered light collected by the collection means; (5) detection means for scanning and measuring the Raman shifted light at frequencies characteristic of disulfide bonds; and (6) quantifying means for determining Raman signal intensity for the disulfide bonds.

As the Raman shift is independent of the wavelength of incident light used, any strong and fairly monochromatic light source can be used in this technique. Thus, for example, the means for generating light can be a laser light source; alternatively, other means include, but are not limited to, light sources that generate monochromatic light, and any other light projection system. Various delivery means and collection means can be used, including, for example, optical components for directing a beam of light from the light source to the nail to be measured, either in situ or as a nail clipping, and for collecting the scattered light. The collected scattered light can be spectrally selected, for example, using a Raman spectrometer that separates the Raman scattered light from Rayleigh scattered light. Thus, the spectrally selective system can comprise various optical components, including, but not limited to, prisms, grating monochromators, and filters such as holographic filters, dielectric filters, acousto-optic filters, combinations thereof, and the like. The light detection system is capable of measuring the intensity of the Raman scattered light as a function of frequency in the frequency range of interest, i.e., at 510 $cm^{-1}$ for detecting the level of disulfide bonding in the nail sample. Components within the light detection system include, but are note limited to, a photomultiplier apparatus, photodiodes, devices such as a charge coupled device (CCD) detector array, anintensified CCD detector array, and the like. Preferably the light detected by the light detection system is converted into a signal that can be displayed visually, for example, on a computer monitor or the like, or is converted into other digital or numerical formats. The resultant Raman signal intensities are preferably analyzed via a quantifying means such as a quantifying system, which may be calibrated, for example, by comparison with spectra obtained from other samples of interest or other peaks on the same sample. In some embodiments, the quantifying system is a computer that comprises spectral data acquisition software installed so that spectral analysis can be manipulated, for example, to remove background noise and the like. For further details on exemplary components that can be included in a Raman spectroscopy apparatus for measurements of level of sulfur bonding, particularly disulfide bonding, in keratinized tissue samples in situ, see U.S. Pat. Nos. 5,873,831 and 6,205,354, herein incorporated by reference in their entirety.

In another embodiment, FT-IR (Fourier transform-infrared) is used to measure the level of sulfur bonding in a keratinized tissue sample such as nail, hair, or skin, where the keratinized tissue is measured in situ or on a collected keratinized tissue sample. Those skilled in the art recognize that infrared covers a slightly different region of the spectrum than Raman spectroscopy. However methods of configuring the FT-IR apparatus to cover this area of the spectrum are well known in the art.

A number of ways of interpreting spectral data are known in the art and are thus suitable for the diagnostic methods disclosed herein. Thus, for example, spectral data obtained from Raman spectroscopy can be analyzed for differences between control versus test biological samples at any given spectral peak of interest, for example, the peak at 510 cm$^{-1}$ corresponding to disulfide bonds (S-S, gauche-gauche-gauche conformation) and the peaks at about 621 cm$^{-1}$ and 643 cm$^{-1}$ corresponding to carbon sulfide bonds (C-S). At any given spectral peak, the difference between a control and test biological sample can be analyzed based upon a comparison of the width at half maximum height of the peak, the relative peak height, area integration (i.e., area under the peak), combinations thereof, and the like. In some embodiments, the diagnostic assays described herein are based on comparisons of the width at half maximum height (WHM) of the Raman spectral peak that corresponds to disulfide bonds of a keratinized tissue such as nail, hair, or skin (i.e., the peak at about 510 cm$^{-1}$). However, it is recognized that any methodology can be utilized to compare differences in the Raman spectra obtained from keratinized tissue samples, for example, differences occurring at the spectral peak appearing at about 510 cm$^{-1}$.

Those skilled in the art recognize that diagnostic assays can be described in terms of accuracy. The term "accuracy" is intended to mean the total number of results of a given test divided by the number of incorrect results. Incorrect results are a function of error rates present in the assay and include but are not limited to measurement error, user error, reporting error, and the like. Diagnostic assays can be further described in terms of false positive and false negative rates. False positive and false negative rates are generated by comparing the results of an assay against a gold standard. By the term "gold standard" is intended a reference standard that is unlikely to be incorrect or has been traditionally used to define the disease, such as bone mineral density for osteoporosis. False positive and false negative rates affect the sensitivity and specificity of an assay.

The sensitivity of a test is the probability that it will produce a true positive result when used on a diseased population (as compared to a reference or "gold standard"). The sensitivity of a diagnostic test is calculated as: (the number of true positive results)/(the number of true positive results+the number of false negative results). The specificity of a test is the probability that a test will produce a true negative result when used on a non-diseased population (as determined by a reference or "gold standard"). The specificity of a test is calculated as: (the number of true negative results)/(the number of true negative results+the number of false positive results). The sensitivity and specificity of a diagnostic test indicates possible uses within a particular population. For example, high sensitivity tests are useful in screening populations where the disease to be diagnosed is relatively serious and the treatment is relatively inexpensive and readily available because the cost of a failing to detect a diseased patient is high (false negative) and the cost of treating an undiseased patient is low (false positive). Alternatively, high specificity tests are useful in screening populations where the disease is not as serious and the treatment is relatively expensive because the few undiagnosed, diseased patients (false negatives) within the population will not suffer greatly as compared to the unnecessary treatment of many non-diseased patients (false positives). It is routine within the art to adjust the specificity and sensitivity of assays or use variant assays with differing sensitivity and specificity to screen specific populations. The sensitivity of the disclosed methods for the detection of a bone disease such as osteoporosis is at least about 70%, preferably at least about 75%, 80%, 85%, more preferably at least about 90, 91, 92, 93, 94, 95, 96, 97, 98, 99% or more, depending upon the diagnostic method used. Furthermore, the specificity of the present methods for detection is at least about 50%, preferably at least about 60%, 70%, 75%, 80%, more preferably at least about 90, 91, 92, 93, 94, 95, 96, 97, 98, 99% or more, depending upon the diagnostic method used.

Measurements of hardness, modulus, or level of sulfur bonding in a keratinized tissue sample find use in screening any population in need of treatment. Those skilled in the art are routinely able to determine the false negative and false positive rates of these assays. Also, those skilled in the art recognize that statistical measures such as accuracy, specificity, and sensitivity are equally applicable to continuous as well as nominal variables. Thus, the diagnostic methods described herein can be used to assess not only the presence or absence of disease (i.e., nominal variable) but also the extent or severity of disease (i.e., continuous variable).

Those skilled in the art also recognize that results of the individual diagnostic assays disclosed herein can be combined with other assays previously known in the art to further refine the accuracy, specificity, and sensitivity of the diagnosis. Thus, the assays disclosed herein may be used in conjunction with such other diagnostic indicators such as clinical presentation, decrease in bone mineral density, radiographic evidence of osteopenia or vertebral deformity, loss of height, thoracic kyphosis, previous fragility fracture, prolonged corticosteroid therapy, premature menopause, prolonged secondary amenorrhea, primary hypogonadism, chronic disorders associated with osteoporosis (e.g., anorexia nervosa, malabsorption syndromes), maternal history of hip fracture, serum prevalence of C-telopeptide of type I collagen, low calcaneal ultrasonic variables (BUA and SOS), low body mass index, and the like.

Those skilled in the art also recognize that the diagnostic assays described herein may be routinely used for prognostic assays. Specifically, the results of a diagnostic assay (e.g., changes in hardness, modulus, or level of sulfur bonding in a keratinized tissue sample) can be correlated to another variable (or combination of variables) of interest, such as the mean time before death, the recovery rate, the relapse rate, the progression rate, the severity of disease, the treatment response rate, molecular diagnostics, and the like, to predict a clinical outcome. Both historical and contemporaneous data on patients are routinely available. These data may be positively or negatively correlated with changes in hardness, modulus, or level of sulfur bonding of a keratinized tissue sample.

The statistical relationships between the results of the diagnostic assay and a known outcome are useful in generating a correlation coefficient, which indicates the magnitude of a correlation as compared to a random association between variables. See, for example, Zhou et al. (2002) *Statistical Methods in Diagnostic Medicine* (Wiley, New York). Other methods of correlating relationships are known in the art and these methods may all find use in the methods disclosed herein.

In some embodiments, the prognostic assays disclosed herein are used to stratify osteoporosis patients with increased risk of bone fracture. The term "stratify" is intended to mean that a group sharing a common characteristic, such as having osteoporosis, is subdivided into one or more subclasses.

To determine changes in the physical or chemical structure of a keratinized tissue sample and thereby detect (by any method known in the art including but not limited to the assays disclosed and incorporated by reference herein) the presence of bone disease, or stage of bone disease, such as osteoporosis, the signal generated from a test of the physical or chemical structure of a keratinized tissue sample is generally compared to a threshold signal that corresponds to a predetermined cut-off value. In one embodiment, the cut-off value for the detection of a change in hardness, modulus, or level of sulfur bonding in a keratinized tissue sample is the average signal obtained from keratinized tissue samples collected from subjects without bone disease, for example, those without osteoporosis.

Generally, detecting a decrease (relative to a control sample) in the hardness or modulus of a keratinized tissue sample or a decrease in the level of sulfur bonding in a keratinized tissue sample is indicative of a bone disease, or more specifically fragile bones, such as those found in osteoporosis patients. Physicians can use the assays disclosed herein to generate information that can assist in choosing to initiate, change, or increase/decrease therapeutic regimens, as discussed supra. In addition, a physician may use information provided by the assays disclosed herein to confirm or exclude potential diagnoses based on other diagnostic methods including bone mineral density and other diagnostics.

In some embodiments, the keratinized tissue sample is nail, and Raman spectroscopy is utilized to predict the presence or absence of osteoporosis in a subject. In this manner, a Raman spectrum is collected on nails (in situ or nail clippings) of the subject to be tested, and the level of disulfide bonding is detected by analyzing the intensity of the peak at 510 $cm^{-1}$ of the Raman spectrum. As noted above, intensity of this peak can be determined using any method of spectral analysis known in the art. The intensity of this peak represents a bone quality score for the individual and is indicative of the presence or absence of, or risk of developing, osteoporosis. In one embodiment, the intensity of the peak at 510 $cm^{-1}$ of the Raman spectrum for nails is calculated based on the width at half maximum (WHM) value of this peak. A mean WHM value at or above about 35 $cm^{-1}$ is indicative of an individual having a bone mineral density (BMD) T-score of $\leq -1.5$ (as measured by DEXA; see FIG. 5). In accordance with the World Health Organization's definition and categorization of osteoporosis, a BMD T-score of $\leq -1.5$ is indicative of low bone mass, while a BMD T-score of $\leq -2.5$ indicates the presence of osteoporosis. The sensitivity of this diagnostic test to predict a BMD T-score of $\leq -2.5$ (and thus presence of osteoporosis) in a population of 52 women participating in a blind clinical trial was 93.3%, while the specificity of the test to predict this BMD T-score was 95.5% (see Example 2 herein below).

Figure 6:
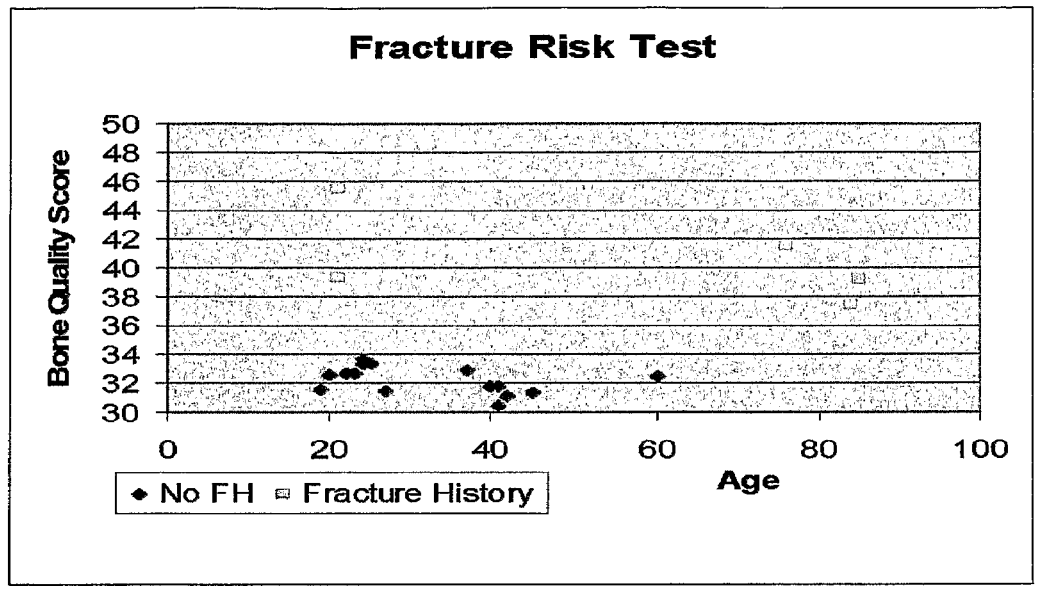
FIG. 6 plots fracture risk history as a function of age and bone quality test score base on WHM for the S-S peak from the Raman spectra for healthy and at risk women.

In other embodiments, a mean WHM value at or above about 35 $cm^{-1}$ for the peak at 510 $cm^{-1}$ of the Raman spectrum for nails is indicative of an individual who is at risk for fracture, for example, fracture associated with a bone disease such as osteoporosis (see FIG. 6). Where an individual tests positive (for example, a mean WHM value at or above about 35 $cm^{-1}$ for the peak at 510 $cm^{-1}$ of the Raman spectrum for nail samples), proactive medical therapy to slow loss of bone mass, disease progression, and to reduce fracture risk can be implemented. One of skill in the art will recognize that subsequent diagnostic assays conducted in a similar manner, e.g., spectral analysis of a keratinized tissue such as nails, for an individual undergoing medical therapy for the bone disease, can provide a means of monitoring treatment efficacy.

The following examples are offered by way of illustration and not by way of limitation.

EXPERIMENTAL

The current noninvasive testing methods for osteoporosis use dual energy x-ray absorptiometry (DEXA) scanners or ultrasound-based scans that measure bone density. These tests require expensive diagnostic equipment and trained personnel, thereby limiting their application.

The diagnostic assays described in Example 1 below represent novel noninvasive diagnostic tests for osteoporosis, which for purposes of this invention are referred to as Bone Quality Tests (BQT). A BQT measures the chemical properties (microarchitecture) of a keratinized tissue such as the nail as opposed to measuring bone density. The BQT is based on the finding that there is a statistically significant difference in the state of the proteins, particularly keratin, between the nails of a healthy person and those of a person with osteoporosis. Thus, the microarchitecture of the nail can be used as an analogue for bone quality.

The BQT is a much simpler methodology, and is potentially more cost effective, than other forms of noninvasive osteoporosis detection methods available today. The BQT can detect osteoporosis fracture risk noninvasively and inexpensively, and will allow primary care practitioners to proactively manage osteoporosis diagnosis and treatment.

Example 1 below demonstrates two means by which the state of proteins in nails can be determined, i.e., nanoindentation and spectroscopic analysis. The latter can be monitored using any spectroscopic methodology, for example, Raman spectroscopy (as demonstrated below), NIR, and FT-IR, as noted elsewhere herein above. Example 2 describes the results of a blind clinical trial undertaken to verify the specificity and sensitivity of the BQT based on Raman spectral analysis.

Example 1

Physical and Chemical Changes in Human Fingernails as Correlates of Bone Disease Two groups of subjects were identified. The first group (n=9) was diagnosed by DEXA (Lunar Prodigy, GE Medical systems), as osteoporotic (T score<−2.5). The second group (n=13) was diagnosed as non-osteoporotic (T score>1.0). All statistical tests correlating disease to various dependent variables were performed using ANCOVA.

Fingernail clippings were obtained from all subjects. The nail apparatus is composed of the nail fold, nail matrix, nail bed, and the hyponychium, which together form the nail plate. This nail plate is produced mainly by the matrix and emerges via the proximal nail fold, while being held in place by the lateral nail fold. It overlays the nail bed and detaches at the point called the hyponychium, or where the free edge of the plate ends. This is where the clipping is taken (see FIG. 1). This area corresponds to the area where high-sulfur keratin, typical of hard keratins, is found. Following their sourcing, samples were stored in sealed specimen jars prior to testing.

Notably, the physical properties of fingernails change when soaked in water, as it becomes soft and flexible. It is thought that the degree of hydration is the most important factor influencing the physical properties of nails because chemically bound water is found in both dry and wet nails. The water-protein interaction changes the keratin structure giving it new mechanical characteristics (Finlay et al. (1980) *Br J. Dermatol.* 103:357; and Wessel et al. (1999) *Biochim Biophys Acta.* 1433:210). This highlights the need to store nail-clipping samples under conditions where they are not exposed to large amounts of water or dehydrated prior to testing. Accordingly, the nails were stored in sealed jars not more than one month before testing.

Experiments performed on nails stored over time confirmed that nails stored in the manner disclosed above maintained the same properties over at least a one month period. Specifically, nail samples were tested weekly over a period of one month for hardness and modulus to confirm that no detectable changes had occurred. In contrast, nail samples that were tested one year after collection exhibited different properties.

Nanoindentation

The nails were trimmed prior to testing to expose the flat mid-section of each nail, and, therefore, reduce the possibility of the curved edges of the nail making premature contact with the indenter. Samples were then attached to aluminium stubs with an epoxy adhesive (part no: 46409, Versachem, Fla., USA).

Nanoindentation experiments were conducted using a laboratory-built machine previously described by Arteaga et al. (1993) *Tribology Intl.* 26:305. For each indentation, the tip was brought into contact with the surface using a load of a few μN. The load was then increased linearly at 0.8 mNs$^{-1}$ up to its maximum value of 120 mN, and then reduced again at the same rate to zero. Every 150 ms during the cycle readings were taken of the displacement of the indenter δ, and the load P, allowing the examination of force-penetration data during both the loading and unloading phases. Consequently, it is possible to produce curves of penetration depth at each force level during the loading and unloading phases. The data for these studies were generated using the Formulae 1-3, supra. A schematic representation of a nanoindentation curve is given in FIG. 2. The collected data are shown in Table 1, and the statistical analysis is shown in Table 2.

TABLE 1

Measurements of modulus and hardness of fingernail clippings.

| Sample | Modulus | Max. Hardness | Min. Hardness | BMD |
|---|---|---|---|---|
| A(1) | 3.43 | 0.247 | 0.236 | 2 |
| A(2) | 3.09 | 0.186 | 0.164 | 2 |
| A(3) | 3.88 | 0.386 | 0.325 | 2 |
| A(4) | 3.38 | 0.23 | 0.201 | 2 |
| A(5) | 3.47 | 0.298 | 0.256 | 2 |
| G2(1) | 3.25 | 0.201 | 0.173 | 2 |
| G2(2) | 3.14 | 0.202 | 0.175 | 2 |
| G2(3) | 3.79 | 0.193 | 0.171 | 2 |
| G2(4) | 3.64 | 0.15 | 0.132 | 2 |
| G2(5) | 3.17 | 0.194 | 0.172 | 2 |
| H2(1) | 2.95 | 0.266 | 0.234 | 2 |
| H2(2) | 4.51 | 0.497 | 0.424 | 2 |
| H2(3) | 4.11 | 0.415 | 0.352 | 2 |
| H2(4) | 6.24 | 0.614 | 0.522 | 2 |
| H2(5) | 3.62 | 0.219 | 0.189 | 2 |
| D(1) | 3.5 | 0.0693 | 0.0645 | 0 |
| D(2) | 3.34 | 0.0626 | 0.0565 | 0 |
| D(3) | 3.26 | 0.0578 | 0.0522 | 0 |
| D(4) | 2.71 | 0.0407 | 0.0369 | 0 |
| E(1) | 4.34 | 0.299 | 0.268 | 0 |
| E(2) | 5.1 | 0.41 | 0.353 | 0 |
| E(3) | 4.62 | 0.36 | 0.31 | 0 |
| E(4) | 4.86 | 0.388 | 0.337 | 0 |
| E(5) | 4.86 | 0.388 | 0.337 | 0 |
| F(1) | 3.51 | 0.273 | 0.237 | 0 |
| F(2) | 3.33 | 0.293 | 0.253 | 0 |
| F(3) | 3.17 | 0.134 | 0.117 | 0 |
| G(1) | 5.12 | 0.212 | 0.187 | 0 |
| G(2) | 5.27 | 0.345 | 0.3 | 0 |
| G(3) | 4.57 | 0.243 | 0.219 | 0 |
| G(4) | 5.27 | 0.275 | 0.239 | 0 |
| G(5) | 5.79 | 0.351 | 0.302 | 0 |
| H(1) | 4.83 | 0.394 | 0.329 | 0 |
| H(2) | 4.12 | 0.261 | 0.226 | 0 |
| H(3) | 4.36 | 0.265 | 0.224 | 0 |
| H(4) | 4.69 | 0.293 | 0.259 | 0 |
| H(5) | 5.4 | 0.359 | 0.298 | 0 |

TABLE 1-continued

Measurements of modulus and hardness of fingernail clippings.

| Sample | Modulus | Max. Hardness | Min. Hardness | BMD |
|---|---|---|---|---|
| I(1) | 2.47 | 0.12 | 0.109 | 0 |
| I(2) | 2.93 | 0.0536 | 0.0506 | 0 |
| I(3) | 3.03 | 0.0756 | 0.0698 | 0 |
| I(4) | 2.8 | 0.135 | 0.122 | 0 |
| I(5) | 3.15 | 0.154 | 0.141 | 0 |
| J(1) | 3.08 | 0.101 | 0.0885 | 0 |
| J(2) | 3.4 | 0.0762 | 0.0706 | 0 |
| J(3) | 2.82 | 0.0609 | 0.056 | 0 |
| J(4) | 2.64 | 0.0782 | 0.0714 | 0 |
| J(5) | 3.83 | 0.125 | 0.112 | 0 |
| K(1) | 4.95 | 0.342 | 0.295 | 0 |
| K(2) | 6.42 | 0.485 | 0.416 | 0 |
| K(3) | 5.48 | 0.415 | 0.356 | 0 |
| K(4) | 6.36 | 0.61 | 0.51 | 0 |
| K(5) | 7.24 | 0.565 | 0.491 | 0 |
| L(1) | 3.45 | 0.309 | 0.263 | 0 |
| L(2) | 3.5 | 0.233 | 0.204 | 0 |
| L(3) | 4.42 | 0.447 | 0.376 | 0 |
| L(4) | 3.94 | 0.31 | 0.27 | 0 |
| N(1) | 0.967 | 0.279 | 0.236 | −3 |
| N(2) | 1.27 | 0.275 | 0.237 | −3 |
| N(3) | 0.933 | 0.145 | 0.131 | −3 |
| N(4) | 1.49 | 0.297 | 0.255 | −3 |
| N(5) | 1.49 | 0.236 | 0.207 | −3 |
| O(1) | 3.86 | 0.179 | 0.158 | −3 |
| O(2) | 2.88 | 0.124 | 0.112 | −3 |
| O(3) | 2.53 | 0.073 | 0.0663 | −3 |
| O(4) | 2.84 | 0.0987 | 0.0903 | −3 |
| O(5) | 2.82 | 0.072 | 0.0672 | −3 |
| P(1) | 1.83 | 0.121 | 0.103 | −3 |
| P(2) | 1.63 | 0.148 | 0.128 | −3 |
| P(3) | 2.67 | 0.0898 | 0.0814 | −3 |
| P(4) | 0.856 | 0.0503 | 0.0472 | −3 |
| Q(1) | 1.41 | 0.0425 | 0.0405 | −3 |
| Q(2) | 1.68 | 0.0768 | 0.0726 | −3 |
| Q(3) | 1.49 | 0.133 | 0.121 | −3 |
| Q(4) | 1.74 | 0.165 | 0.148 | −3 |
| Q(5) | 1.97 | 0.183 | 0.161 | −3 |
| R(2) | 5.06 | 0.376 | 0.324 | −3 |
| R(3) | 5.6 | 0.52 | 0.439 | −3 |
| R(4) | 4.61 | 0.305 | 0.261 | −3 |
| R(5) | 6.12 | 0.638 | 0.52 | −3 |
| S(1) | 3.02 | 0.0996 | 0.0908 | −3 |
| S(2) | 4.47 | 0.37 | 0.324 | −3 |
| S(3) | 3.58 | 0.21 | 0.185 | −3 |
| S(4) | 3.61 | 0.18 | 0.155 | −3 |
| S(5) | 3.81 | 0.31 | 0.263 | −3 |
| T(1) | 3.68 | 0.198 | 0.179 | −3 |
| T(2) | 3.58 | 0.137 | 0.125 | −3 |
| T(3) | 4.01 | 0.295 | 0.251 | −3 |
| T(4) | 2.99 | 0.148 | 0.134 | −3 |
| T(5) | 3.3 | 0.105 | 0.0978 | −3 |
| U(1) | 2.27 | 0.172 | 0.153 | −3 |
| U(2) | 1.21 | 0.122 | 0.114 | −3 |
| U(3) | 3.56 | 0.263 | 0.233 | −3 |
| U(4) | 4.08 | 0.299 | 0.262 | −3 |
| U(5) | 3.2 | 0.138 | 0.126 | −3 |
| V(1) | 4.08 | 0.144 | 0.133 | −3 |
| V(2) | 4.39 | 0.131 | 0.116 | −3 |
| V(3) | 6.23 | 0.458 | 0.398 | −3 |
| V(4) | 4.33 | 0.142 | 0.134 | −3 |
| V(5) | 3.75 | 0.277 | 0.242 | −3 |

TABLE 2

Statistical analysis of collected data.

High BMD Group

| | | | |
|---|---|---|---|
| mean modulus | 3.711333333 | mean hardness | 0.267467 |
| standard deviation | 0.81434344 | standard deviation | 0.121951 |

TABLE 2-continued

Statistical analysis of collected data.

Normal BMD Group

| | | | |
|---|---|---|---|
| mean modulus | 4.193414634 | mean hardness | 0.238365 |
| standard deviation | 1.162156637 | standard deviation | 0.139288 |

Low BMD Group

| | | | |
|---|---|---|---|
| mean modulus | 3.044093023 | mean hardness | 0.192416 |
| standard deviation | 1.413736299 | standard deviation | 0.117027 |

All Non-Osteoporotic

| | | | |
|---|---|---|---|
| mean modulus | 4.064285714 | mean hardness | 0.24616 |
| standard deviation | 1.094289071 | standard deviation | 0.134947 |

Mean elastic moduli and hardness results for the two sets of fingernails are included below in Table 3.

TABLE 3

Mean moduli and hardness (and standard deviations) of fingernails sourced.

| Subject Group | Moduli (GPa) | Hardness (GPa) |
|---|---|---|
| Osteoporotic | 3.0 (±1.5) | 0.19 (±0.12) |
| Healthy | 4.1 (±1.1) | 0.23 (±0.14) |

The mean moduli of fingernails from patients with low BMD are approximately 25% lower than those with normal BMD. The difference in mean modulus between the groups was found to be 1.1 GPa, which only approached significance at 5% level (p=0.147) due to a lack of power (small n) within the test.

Raman Spectroscopy

For Raman analysis, four fingernail samples from each group were analysed to ascertain if there was disparity between groups, and to detect osteoporotic-induced changes in keratinized tissue. Micro Raman spectra were obtained using a Dilor Labram 01 instrument. Excitation was by red laser operating at 632.81 nm. Spectra were obtained by performing 20 scans, to improve the signal-to-noise ratio, each with a laser exposure time of 50 seconds. The same operating procedure was repeated for all samples in order for the resultant spectra to show only the differences between the osteoporotic and non-osteoporotic tissue. Spectra were recorded from 300 $cm^{-1}$ to 1800 $cm^{-1}$ for identification of all the characteristic peaks in human nail. The interval from 300 $cm^{-1}$ to 700 $cm^1$ was selected for comparison. Normalization of all acquired spectra was carried out to facilitate the comparison and to highlight differences between groups.

Figure 3:
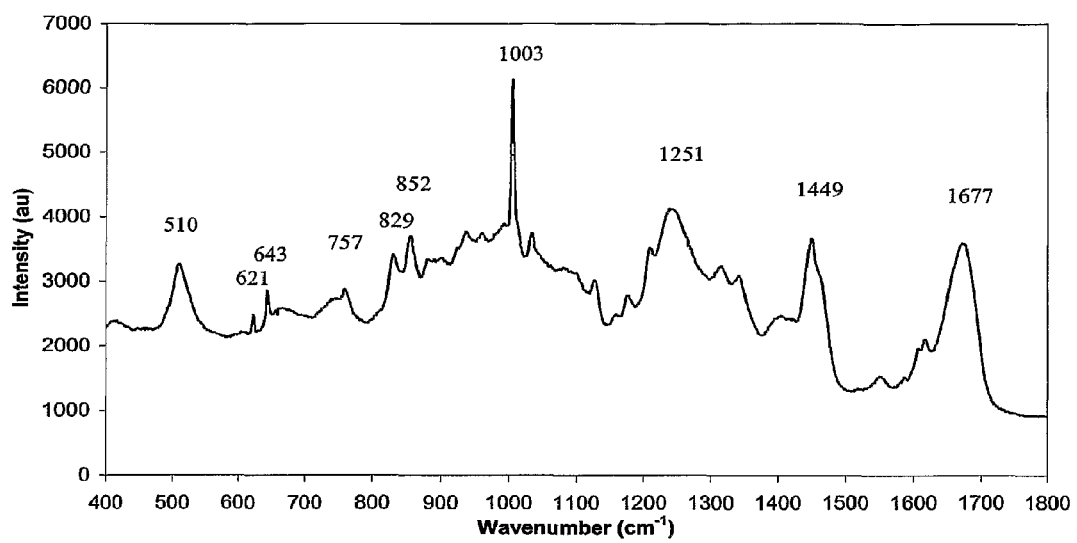
FIG. 3 shows a typical Raman spectrum of the human nail from 300 $cm^{-1}$-1800 $cm^{-1}$.

FIG. 3 shows the typical Raman spectrum of human nail between 300 $cm^{-1}$ and 1800 $cm^{-1}$. The major spectral peaks of human nail include the amide band at 1677 $cm^{-1}$ indicating that nail keratin is predominantly α-helical, the methylene ($CH_2$) deformation band at 1450 $cm^{-1}$ and the amide [ν(CN)] band at 1251 $cm^{-1}$. In the 1000 $cm^{-1}$ to 1200 $cm^1$ region the strongest band occurs at 1006 $cm^{-1}$, corresponding to the C—C stretching vibration of the aromatic ring in the phenylalanine side chain. However, it is the lower region of the spectrum that is of most concern in this study. The area between 700 $cm^1$ and 300 $cm^{-1}$ contains the spectral information about the sulfur bonding in fingernails. The relative intensities of the S-S and C-S stretching vibrations give a good indication of the amount of sulfur present and allow determination of the structural configuration of the S—S bond. FIG. 3 shows the peak at 510 $cm^{-1}$ representing the disulfide bonding [ν (SS)]. Lesser peaks at 621 $cm^{-1}$ and 645 $cm^{-1}$ represent carbon sulfide bonding [ν (CS)].

Figure 4:
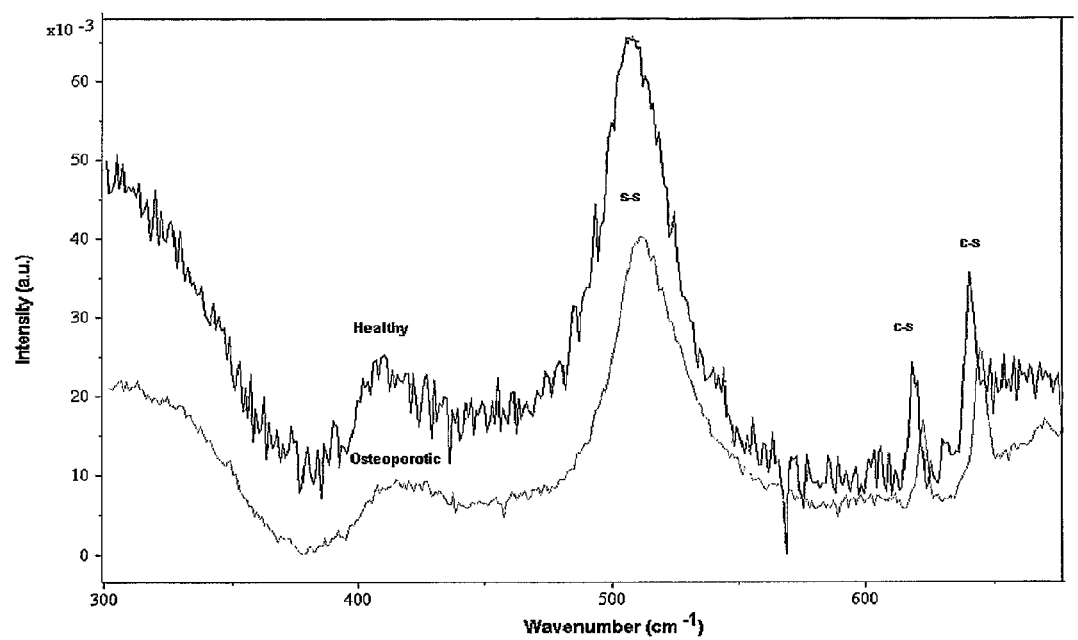
FIG. 4 shows two Raman spectra, one from a non-osteoporotic (healthy) individual (top) and one from an osteoporotic individual (bottom).

FIG. 4 shows normalized Raman spectra for an osteoporotic and non-osteoporotic nail on the same scale. Two main differences between osteoporotic and normal nails were observed. The disulfide bond (S—S, gauche-gauche-gauche conformation) peak for healthy nail at 510 $cm^{-1}$ was much sharper than for the osteoporotic nail and the width of the S-S peak in osteoporotic nail was found to be larger than the healthy nail. Therefore, the disulfide bond content of the nails sourced from osteoporotic patients was lower than those from healthy patients. Table 4 shows that this difference in mean width at half maxima for the S—S peak from the two sets of nails is statistically significant (ANCOVA).

TABLE 4

Raman spectroscopy results for osteoporotic versus non-osteoporotic nail.

| Width at half maxima for the S-S peak | ($cm^{-1}$) Minimum | ($cm^{-1}$) Maximum | ($cm^{-1}$) Mean | Std. Deviation |
|---|---|---|---|---|
| Non-osteoporotic | 25.00 | 30.70 | 27.68 | 2.39 |
| Osteoporotic | 37.50 | 42.30 | 39.20 | 2.12 |

There was also a shift in the carbon sulfide bond (C—S) peak at about 621 $cm^{-1}$ and 643 $cm^{-1}$ as shown by the higher wave numbers detected for the C—S bonds in osteoporotic nail.

In protein spectra the C—S vibrational band originates from methionine, cysteine and cystine. Since methionine content in human nail is negligible, the C—S and S—S bonds shown must have originated from cysteine and cystine (Marshall et al. (1996) *BMJ* 312:1254). While not being bound by any particular mechanism or theory of action, the shift in the carbon sulfide bonding may be due to the change of the sulfur content in the nails since it is known that the C—S stretching vibration is dependent on the conformation of its side chains.

Example 2

Verification of Bone Quality Test Based on Raman Spectral Analysis of Nails

The World Health Organization (WHO) defines osteoporosis as "a skeletal disorder characterized by compromised bone strength predisposing a person to an increased risk of fracture." The WHO uses the bone mineral density (BMD) T-score as the standard for identifying the osteoporotic condition. To obtain the T-score, an individual's BMD result (for example, from DEXA) is compared with the BMD results from healthy 25-to 35-year-old adults of the same sex and ethnicity. The standard deviation (SD) is the difference between your BMD and that of the healthy young adults. This result is the "T-score." Positive T-score values are indicative of bone that is stronger than normal; negative T-score values are indicative of bone that is weaker than normal. According to the WHO, osteoporosis is categorized based on the following bone mineral density levels:

A T-score within 1 SD (+1 or −1) of the young adult mean indicates normal bone density;

A T-score of 1 to 2.4 SD below the young adult mean (−1 to −2.5 SD) indicates low bone mass;

A T-score of 2.5 SD or more below the young adult mean (greater than −2.5 SD) indicates the presence of osteoporosis.

In general, the risk for bone fracture doubles with every SD below normal. Thus, for example, a person with a T-score of −1 has twice the risk for bone fracture as a person with a normal BMD. A person with a T-score of −2 has four times the risk for bone fracture as a person with a normal BMD. When this information is known, people with a high risk for bone fracture can be treated with the goal of preventing future fractures.

The present example provides the results of a blind clinical trial that was carried out to identify women, based on the BQT, who were defined as having osteoporosis using the World Health Organization (WHO) definition for this condition (i.e., a BMD T-score of less than (i.e., more negative than) or equal to −2.5 (e.g., −3.0). The sample size was 52 patients, and the BQT data were obtained using Raman spectroscopy of fingernail samples collected from these patients, and analyzing for differences in the Raman spectral peak at 510 cm$^{-1}$ (i.e., the S—S peak).

Figure 5:
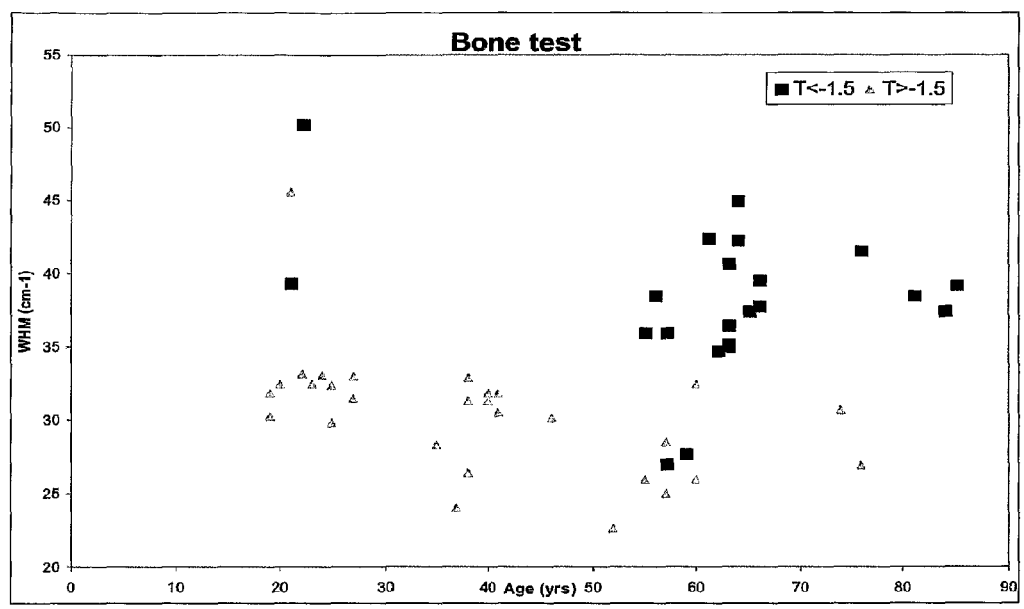
FIG. 5 plots T-score as a function of age and bone quality test score based on the width at half maxima (WHM) for the S-S peak from the Raman spectra for patients in the blind clinical trial referred to in Example 2.

In this manner, fingernail clippings from these subjects were examined using Raman spectroscopy (spectra obtained with a Dilor Labram 01 instrument) in a manner similar to that described in Example 1. For this study, the width at half maxima (WHM) for the S-S peak from the Raman spectrum was determined for nails collected from each individual, and the relationships between T-score and age and T-score and WHM value in order to evaluate T-score as a function of WHM and age. Results are shown in FIG. 5. Table 5 shows the number of non-osteoporotic and osteoporotic patients that had a high WHM value (i.e., 35 cm$^{-1}$ or greater) and low WHM value (i.e., about 34 cm$^{-1}$ or less).

TABLE 5

Distribution of non-osteoporotic and osteoporotic patients based on WHM value obtained from BQT using Raman spectral analysis of nails.

| | Non-Osteoporotic | Osteoporotic |
|---|---|---|
| WHM High | 1 | 28 |
| WHM Low | 21 | 2 |

Sensitivity of the BQT (i.e., the proportion of patients who tested positive and have osteoporosis) was 93.3% (i.e., 28/30). Specificity of the BQT (i.e., the proportion of patients who tested negative and do not have osteoporosis) was 95.5% (i.e., 21/22). Table 6 shows the comparative sensitivity and specificity of the BQT and other diagnostic tests to predict osteoporosis (i.e., a T-score≤−2.5)

TABLE 6

Comparison of BQT with other diagnostic tests to predict T score ≤−2.5

| Test Method | Sensitivity | Specificity |
|---|---|---|
| BQT | 93.3% | 95.5% |
| QUS | 88%-100% | 47% |
| pDXA | 94% | 69% |
| SCORE | 65.7% | 61.1% |
| Questionnaire | 93.3% | 46.4% |

For information regarding the use of these other diagnostic tests as predictors of osteoporosis, see, for example, Naganathan et al. (1999) *Med. J. Aust.* 171:297-300 (quantative heel ultrasound (QUS)); Ross and Simon (1998) *J. Bone Miner. Res.* 23(suppl):S601, Rea et al. (2000) *Osteoporos Int.* 11(8):660-8, and Rea et al. (2000) *J. Bone Miner. Res.* 15(3): 564-74 (pDXA); Orthopaedic Nursing 24(1):33-39 (SCORE), and Cadarette et al. (2000) *C.M.A.J.* 162(9):1289-94 (Questionnaire).

These results indicate that a positive result on the BQT is equivalent to a DEXA T-score of −2.5 or less, and treatment should be considered accordingly.

In another assessment of the predictive value of the BQT, the fracture risk as a function of the bone quality score and age was determined for a subset of the women participating in this trial. As can be seen from FIG. 6, women with fracture histories have very different bone quality scores (WHM score value over about 36 cm$^{-1}$) from women with no fracture history (WHM score value below about 34 cm$^{-1}$).

Thus Raman spectroscopy of nails, either in situ or as nail clippings, can assess fracture risk in a more rapid and less expensive manner that avoids potential problems associated with radiation assessment. Further, a desktop Raman spectroscopy apparatus such as that described in Example 3 below, could be made readily available to practitioners to support mass screening of subjects for the presence or absence of a disease such as osteoporosis, to follow treatment efficacy of individuals having or at risk of developing a bone disease such as osteoporosis, and to predict fracture risk. A reduction in fractures based on more screening and preventative treatment could have significant health and economic benefits worldwide and expand the osteoporosis preventative drug market considerably.

Example 3

Raman Spectroscopy Apparatus for Assessing Osteoporosis and Fracture Risk

Figure 7:
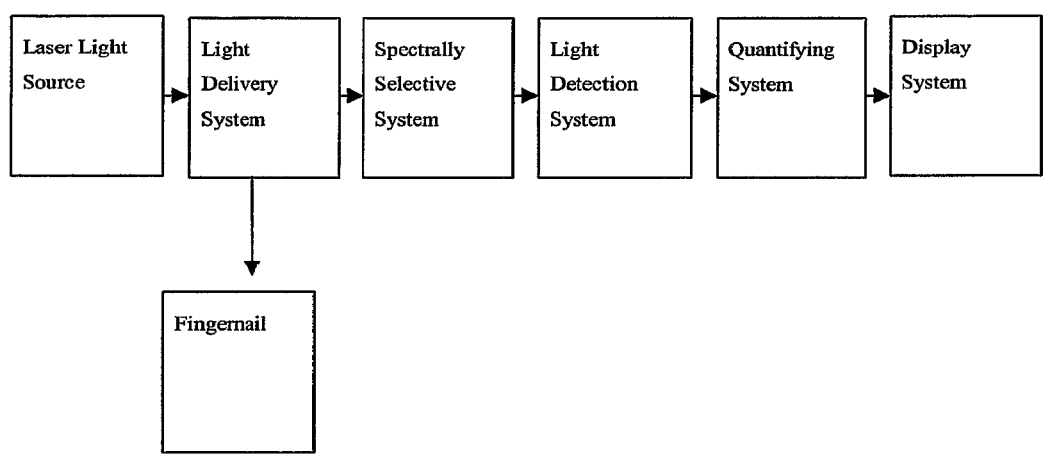
FIG. 7 outlines the components of a Raman spectroscopy apparatus for use in obtaining Raman spectra from keratinized tissue samples such as nails either in situ or as nail clippings for a subject undergoing testing for a bone disease such as osteoporosis.

Any commercially available Raman spectroscopy system can be utilized in the diagnostic assays described herein. FIG. 7 illustrates the main components that can be found within such a system for use in conducting Raman spectral analysis of a keratinized tissue such as nail, either in situ or as nail clippings. The components can be assembled as part of an individual package, or can be constructed as multiple units that are integrated for operation and spectral analysis. In order to collect the spectral data, a probe is placed against the nail of a subject, for example, an intact fingernail of a finger, and a beam of light from the light source is delivered to the nail surface, for example, by pressing a button on the apparatus. The light delivery time can vary, but can be as short as 2-5 seconds. Following spectral selection for Raman scattered light, detection of the Raman scattered light, and quantification, the spectral result is displayed, for example, on a screen, and can then be written to a chip with a data stamp.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

The invention claimed is:

1. A method of diagnosing a bone disease in a subject, the method comprising:
    obtaining a keratinized tissue sample from a subject;
    using a Raman spectrometer to obtain a Raman signal and a Rayleigh scattered light signal from the sample;
    separating the Raman signal from the Rayleigh scattered light signal;
    using a computer to normalize the Raman signal, thereby producing a normalized Raman signal;
    using the computer to measure a level of sulfur bonding indicated by at least one peak in the normalized Raman signal to make a positive or negative diagnosis of the bone disease; and
    using the computer to generate an output that is indicative of the positive or negative diagnosis of the bone disease.

2. The method of claim 1, wherein the keratinized tissue sample is a nail clipping.

3. The method of claim 1, wherein the Raman signal covers between 300 $cm^{-1}$ and 1800 $cm^{-1}$.

4. The method of claim 1, wherein obtaining the Raman signal comprises using a laser light source.

5. The method of claim 1, wherein the at least one peak is at 510 $cm^{-1}$.

6. The method of claim 5, wherein the measuring is accomplished by a technique that is selected from a group consisting of: comparison of a width at half maximum of the peak, comparison of a relative peak height, and area integration under the peak.

7. The method of claim 5, wherein the bone disease is osteoporosis.

8. The method of claim 7, wherein the measuring is accomplished by area integration under the peak.

9. The method of claim 7, wherein the measuring is accomplished by comparison of a relative peak height.

10. The method of claim 1, wherein the bone disease is osteoporosis.

* * * * *